(12) United States Patent
Zhang et al.

(10) Patent No.: US 9,028,512 B2
(45) Date of Patent: May 12, 2015

(54) MATERIAL REMOVAL DEVICE HAVING IMPROVED MATERIAL CAPTURE EFFICIENCY AND METHODS OF USE

(71) Applicant: Covidien LP, Mansfield, MA (US)

(72) Inventors: Zhiyong Zhang, Edina, MN (US); John Robert Moberg, Elk River, MN (US); Hussain S. Rangwala, Orange, CA (US); Thomas John McPeak, Shakopee, MN (US); William Joseph Whealon, Chaska, MN (US); Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 171 days.

(21) Appl. No.: 13/622,073

(22) Filed: Sep. 18, 2012

(65) Prior Publication Data

US 2013/0018397 A1    Jan. 17, 2013

Related U.S. Application Data

(63) Continuation of application No. 12/964,544, filed on Dec. 9, 2010, now abandoned.

(60) Provisional application No. 61/285,768, filed on Dec. 11, 2009.

(51) Int. Cl.
*A61B 17/22* (2006.01)
*A61B 17/3207* (2006.01)
*A61B 17/00* (2006.01)
*A61B 17/32* (2006.01)

(52) U.S. Cl.
CPC . *A61B 17/320783* (2013.01); *A61B 17/320758* (2013.01); *A61B 2017/00685* (2013.01); *A61B 2017/320032* (2013.01); *A61B 2017/320064* (2013.01); *A61B 2017/320791* (2013.01)

(58) Field of Classification Search
USPC ............................................. 606/159; 604/22
See application file for complete search history.

(56) References Cited

U.S. PATENT DOCUMENTS

| | | |
|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

Office action for Russian Patent Application No. 2012121843, dated Sep. 24, 2013, 9 pages, with English translation.

(Continued)

*Primary Examiner* — Tuan V Nguyen
(74) *Attorney, Agent, or Firm* — Alana T. Bergman, Esq.

(57) ABSTRACT

An improved atherectomy catheter includes a part for propelling fluid distally in a tissue collection chamber. The part includes a drive shaft having a proximal end and a distal portion, and a propeller attached to the distal portion of the drive shaft.

15 Claims, 13 Drawing Sheets

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |

(56) References Cited

U.S. PATENT DOCUMENTS

| | | |
|---|---|---|
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |

(56) References Cited

U.S. PATENT DOCUMENTS

| | | |
|---|---|---|
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |

(56) References Cited

U.S. PATENT DOCUMENTS

| | | |
|---|---|---|
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2011/0160758 A1 | 6/2011 | Straub |

(56) References Cited

U.S. PATENT DOCUMENTS

FOREIGN PATENT DOCUMENTS

| | | | |
|---|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 02-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |

OTHER PUBLICATIONS

Amplatz Coronary Catheters, posted: Feb. 25, 2009, [online], [retrieved on Mar. 29, 2011], retrieved from the Cardiophile MD website using Internet <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiophile MD website using Internet <URL:http://cardiophile.org/2009/02/judkins-left-coronary-catheter.html> (3 pages).
International Search Report and Written Opinion issued in counterpart PCT Application No. PCT/US2010/059740 dated May 17, 2011, 17 pages.
Communication pursuant to Rules 161(1 and 162 EPC from EP 10796232.6 dated Jul. 18, 2013, 2 pages.
Notice for Reasons for Rejections for JP 2012-543286 dated Aug. 20, 2013, 7 pages, with English translation.
KIPO's Notice of Preliminary Rejections (English Translation) for 10-2012-7017894 dated Sep. 26, 2013, 6 pages.
Canadian Office action for Application No. 2,783,301 dated Oct. 11, 2013, 2 pages.
Chinese Office action for Application No. 201080055972.0 dated Apr. 8, 2014, 19 pages with English translation, Beijing, China.
Patent Examination Report No. 1 for Australian Application No. 2010328078 dated Oct. 4, 2012, 3 pages.
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).
Japanese Office action for Application No. 2013-250793 dated Sep. 8, 2014, 7 pages with English translation.

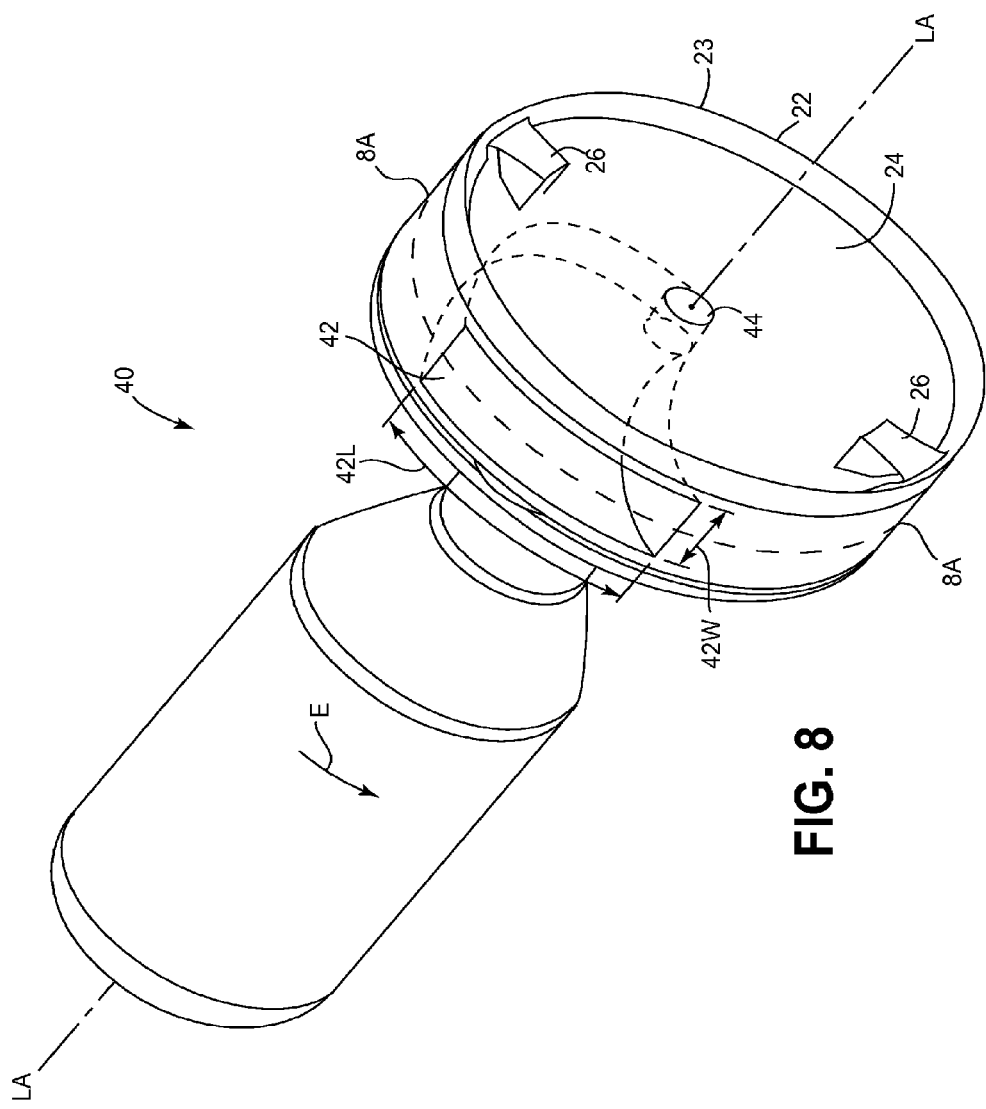

MATERIAL REMOVAL DEVICE HAVING IMPROVED MATERIAL CAPTURE EFFICIENCY AND METHODS OF USE

This application is a continuation of U.S. patent application Ser. No. 12/964,544, filed Dec. 9, 2010, now abandoned, which claims the benefit of U.S. Provisional Patent Application No. 61/285,768, filed Dec. 11, 2009, entitled "Material Removal Device Having Improved Material Capture Efficiency and Methods of Use", the contents of each of which are hereby incorporated by reference herein.

FIELD OF THE INVENTION

The present invention relates to catheters used to remove material from a site in a body lumen. More particularly, this invention pertains to catheters capable of capturing the material removed from the site.

BACKGROUND OF THE INVENTION

Atherosclerosis is a progressive disease of the vascular system whereby atheroma is deposited on the inner walls of blood vessels. Over time atheromatous deposits can become large enough to reduce or occlude blood flow through the vessels, leading to symptoms of low blood flow such as pain in the legs (on walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods, however these methods undesirably tear and stretch the vessel, causing scar formation in a high percentage of patients. Such scar tissue (restenotic material), once formed, blocks flow in the vessel and often needs to be removed. The deposits can be pulverized using lasers and other methods however pulverization alone of atheromatous material allows microemboli to flow downstream and lodge in distal vascular beds, further compromising blood flow to the tissue affected by the disease. Atherectomy catheters can be used to remove atheromatous deposits from the blood vessel and can present an ideal solution when the atheromatous debris removed from the vessel is captured and removed from the body.

One problem that occurs when removing material from a blood vessel is that material fragments may be created by the removal means, in some cases by a cutter, and such fragments may be left in the body where they can embolize and cause problems. It is desirable to remove from the body all material fragments created at the time of material removal from a vessel wall. Some catheters are designed to remove material from the body by directing material particles into a collection chamber however these collection efforts are not always 100% effective. Improved particle collection means are needed.

SUMMARY OF THE INVENTION

The invention provides an atherectomy catheter, comprising: a body having an opening; a rotatable shaft coupled to the body; a tissue collection chamber coupled to the body and positioned distal to the cutting element; a cutting element coupled to the rotatable shaft, the cutting element having a cutting edge; and a lumen configured to direct fluid into the tissue collection chamber.

The invention provides an atherectomy catheter, comprising: a body having an opening; a rotatable shaft coupled to the body; a tissue collection chamber coupled to the body and positioned distal to the cutting element; a cutting element coupled to the rotatable shaft, the cutting element having a cutting edge; and a part for propelling fluid distally in the tissue collection chamber, the part being selected from the group consisting of: (i) a drive shaft having a proximal end and a distal portion, the proximal end being attached to the cutting element and a propeller being attached to the distal portion; and (ii) a paddle attached to the cutting element.

The invention provides a method of recirculating fluid in an atherectomy catheter comprising: providing an atherectomy catheter, the atherectomy catheter comprising: a body having an opening; a rotatable shaft coupled to the body; a tissue collection chamber coupled to the body and positioned distal to the cutting element, the tissue collection chamber having vent holes; a cutting element coupled to the rotatable shaft, the cutting element having a cutting edge; and moving fluid out of the tissue collection chamber through the vent holes such that a negative pressure is created inside the tissue collection chamber and this negative pressure causing fluid to enter the tissue collection chamber through the opening of the body of the catheter.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft, the cutting element having a cutting edge; and a lumen configured to direct fluid into the tissue collection chamber; placing the catheter in the body lumen; and moving the catheter in the body lumen to contact the cutting element with the material in the body lumen.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft, the cutting element having a cutting edge; and a part for propelling fluid distally in the tissue collection chamber, the part being selected from the group consisting of: (i) a drive shaft having a proximal end and a distal portion, the proximal end being attached to the cutting element and a propeller being attached to the distal portion; and (ii) a paddle attached to the cutting element; placing the catheter in the body lumen; and moving the catheter in the body lumen to contact the cutting element with the material in the body lumen.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 8 illustrates an isometric view of another embodiment of a cutting element.

DETAILED DESCRIPTION

Figure 1:
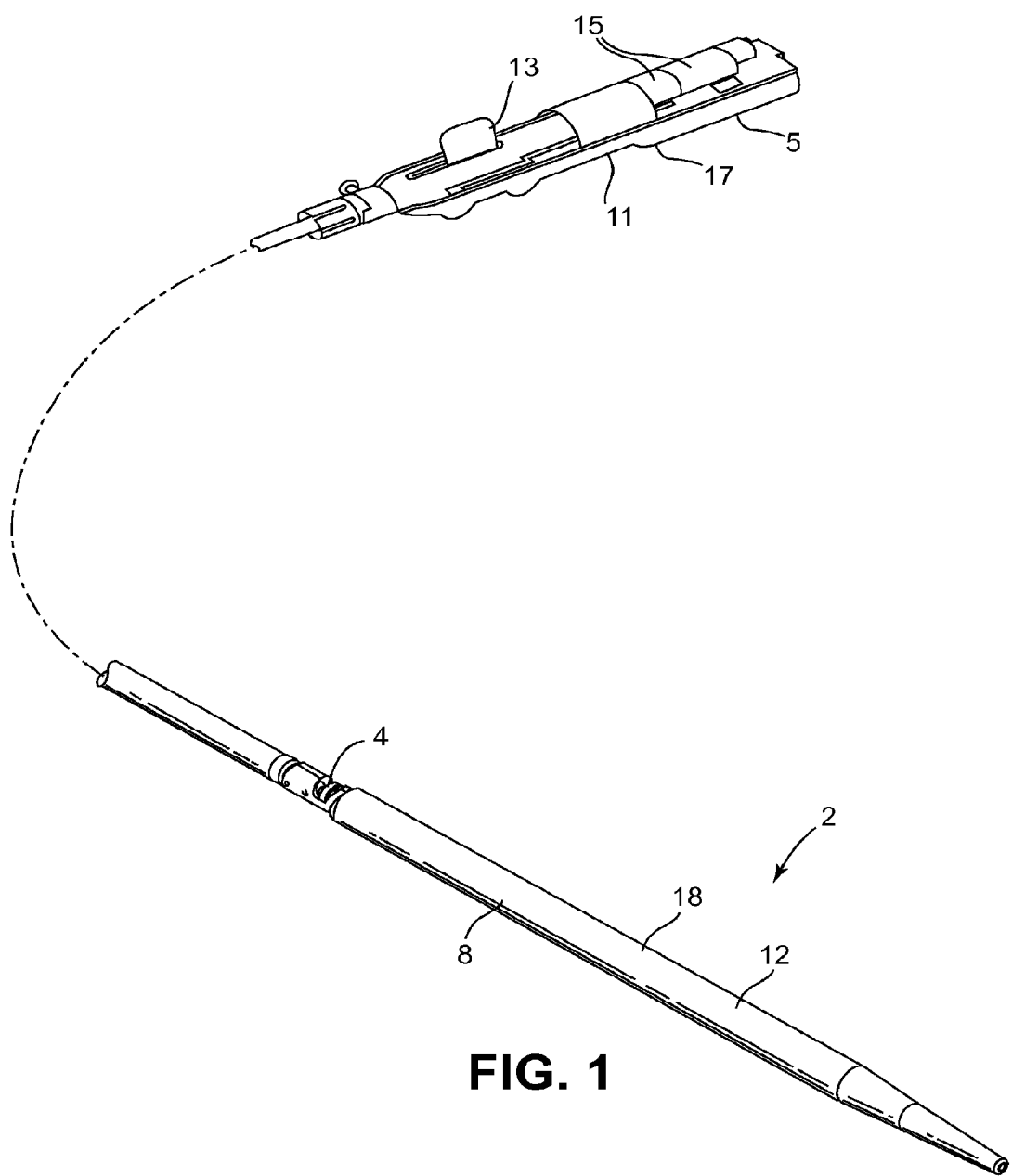
FIG. 1 illustrates a partial isometric view of an atherectomy catheter.
Figure 2:
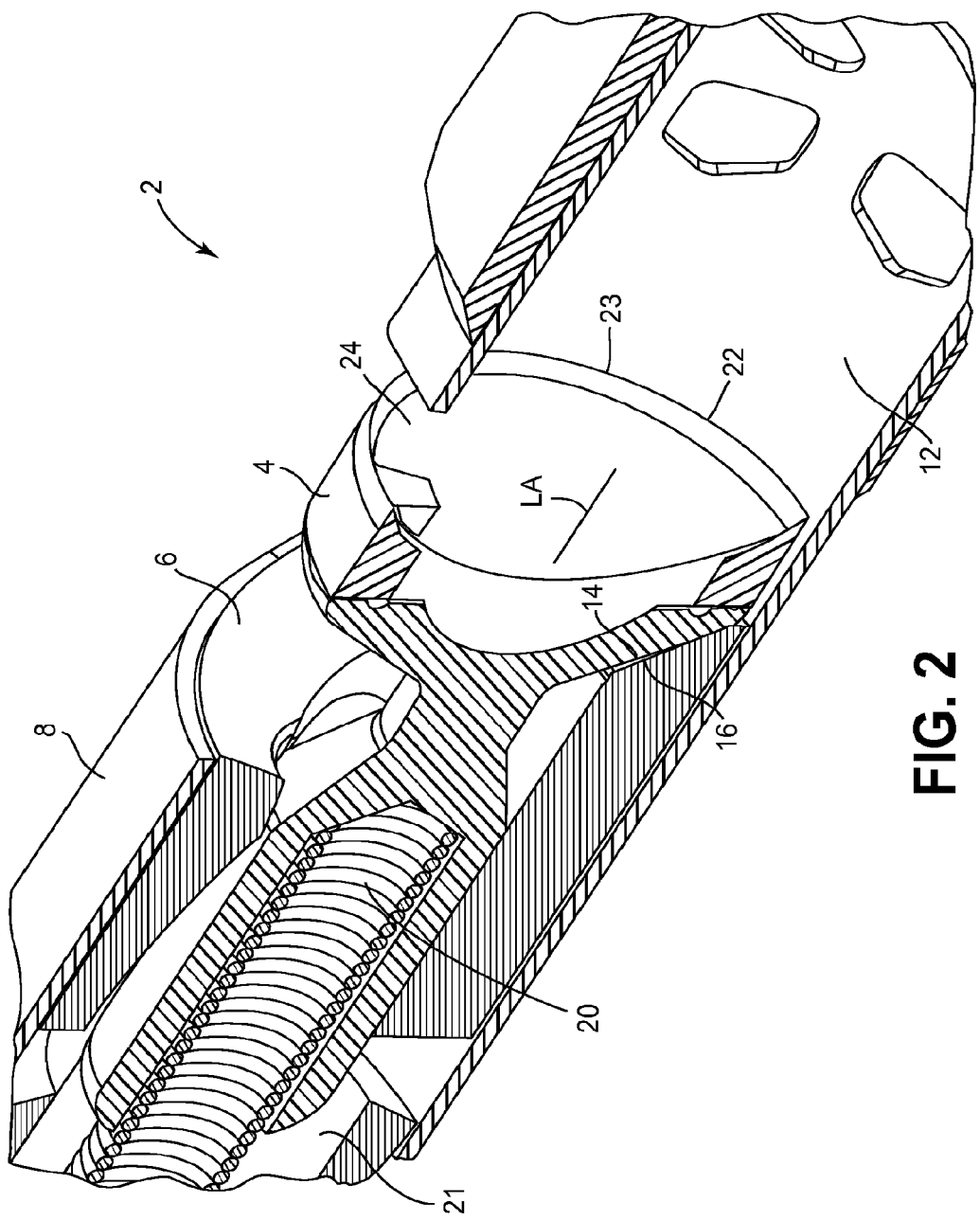
FIG. 2 illustrates an isometric cross-sectional view of a portion of the atherectomy catheter illustrated in FIG. 1 with a cutting element in a stored position.
Figure 3:
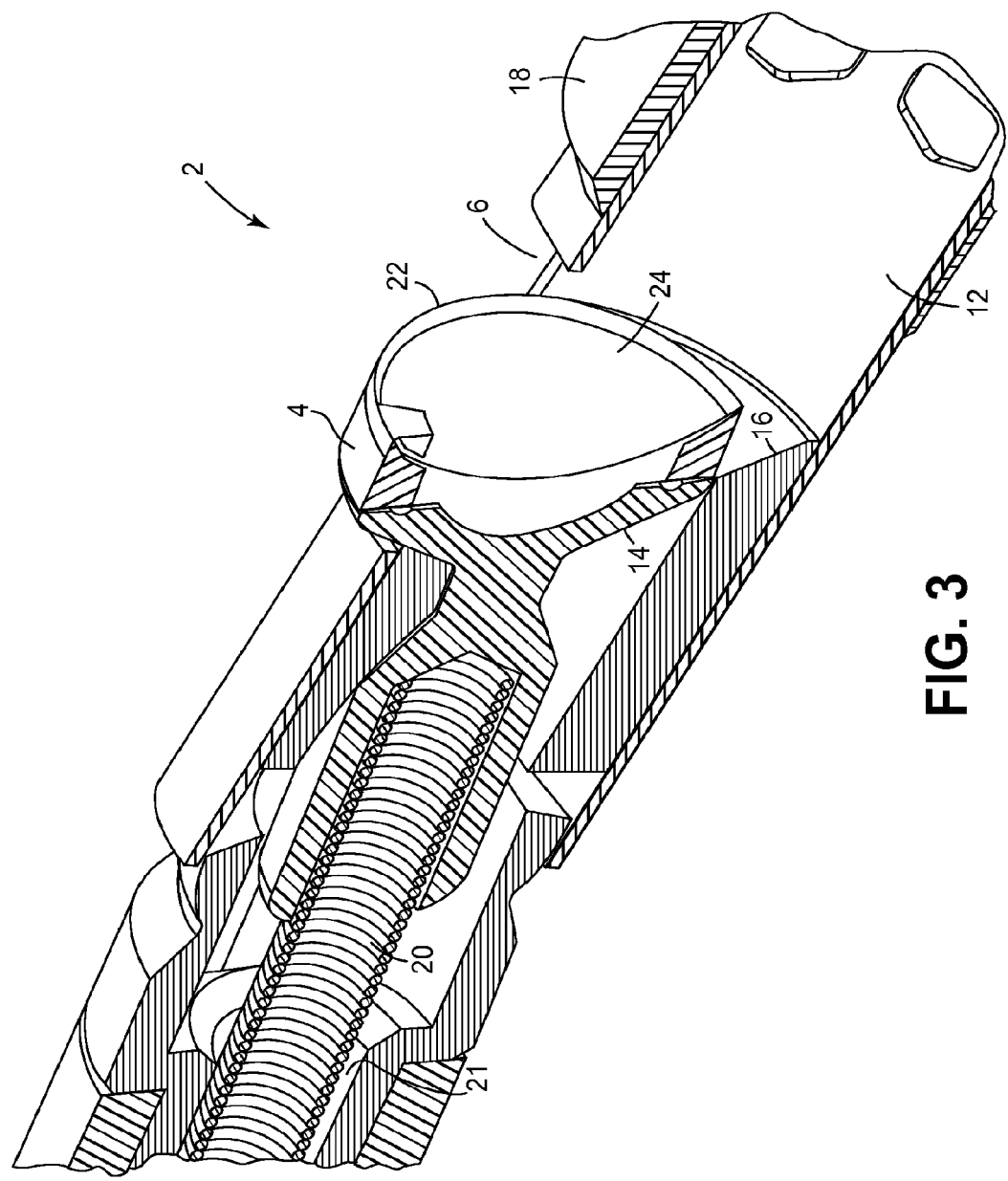
FIG. 3 illustrates an isometric cross-sectional view of a portion of the atherectomy catheter illustrated in FIG. 1 with a cutting element in a working position.

The invention provides an atherectomy catheter, comprising: a body having an opening; a rotatable shaft coupled to the body; a tissue collection chamber coupled to the body and positioned distal to the cutting element; a cutting element coupled to the rotatable shaft, the cutting element having a cutting edge; and a lumen configured to direct fluid into the tissue collection chamber. In one embodiment, the lumen directs fluid in a distal direction into the tissue collection chamber. In one embodiment, the cutting element has a cup-shaped surface, the cup-shaped surface being configured to re-direct tissue cut by the cutting edge in a distal direction when the cup-shaped surface moves in the distal direction. In one embodiment, the lumen has a distal opening on the cup-shaped surface of the cutting element. In an embodiment, the lumen comprises a first lumen portion in the cutting element and a second lumen portion in the rotatable shaft. In one embodiment, the distal opening is positioned at a longitudinal axis of the cutting element. In an embodiment, the lumen has a distal opening and the distal opening is not positioned on the cup-shaped surface of the cutting element. In one embodiment, the distal opening is positioned adjacent to the cup-shaped surface of the cutting element.

In an embodiment, a fluid source that supplies fluid to the lumen is attached to a proximal portion of the catheter. In one embodiment, the fluid supplied by the fluid source is a saline solution. In one embodiment, the fluid supplied by the fluid source comprises a radiopaque substance.

In an embodiment, a proximal opening of the lumen is positioned at a distal portion of the catheter but proximal of the cup-shaped surface of the cutting element. In one embodiment, the proximal opening is positioned on the rotatable shaft. In one embodiment, the rotatable shaft comprises two or more proximal openings of the lumen. In an embodiment, the rotatable shaft comprises an impeller proximal of the proximal opening, the impeller forcing fluid into the proximal opening when the rotatable shaft is rotated. In one embodiment, the impeller has 1 to 10 turns. In one embodiment, the lumen has a distal opening on the cup-shaped surface of the cutting element. In an embodiment, the distal opening is positioned at a longitudinal axis of the cutting element.

In one embodiment, a proximal opening of the lumen is positioned on the cutting element. In an embodiment, the proximal opening is positioned at an outer edge of the cutting element. In one embodiment, the cutting element has a cup-shaped surface, the cup-shaped surface being configured to re-direct tissue cut by the cutting edge in a distal direction when the cup-shaped surface moves in the distal direction, and the lumen has a distal opening on the cup-shaped surface of the cutting element. In an embodiment, the distal opening is positioned at a longitudinal axis of the cutting element.

In an embodiment, the tissue collection chamber comprises vent holes. In one embodiment, the tissue collection chamber comprises 10 to 200 vent holes. In an embodiment, the vent holes have a diameter of from 25 to 200 microns. In an embodiment, the cutting element is movable between a stored position and a cutting position relative to the opening.

The invention provides an atherectomy catheter, comprising: a body having an opening; a rotatable shaft coupled to the body; a tissue collection chamber coupled to the body and positioned distal to the cutting element; a cutting element coupled to the rotatable shaft, the cutting element having a cutting edge; and a part for propelling fluid distally in the tissue collection chamber, the part being selected from the group consisting of: (i) a drive shaft having a proximal end and a distal portion, the proximal end being attached to the cutting element and a propeller being attached to the distal portion; and (ii) a paddle attached to the cutting element. In one embodiment, the cutting element has a cup-shaped surface, the cup-shaped surface being configured to re-direct tissue cut by the cutting edge in a distal direction when the cup-shaped surface moves in the distal direction. In an embodiment, the part for propelling fluid distally in the tissue collection chamber is selected from the group consisting of: (i) a drive shaft having a proximal end and a distal portion, the proximal end being attached to the cup-shaped surface of the cutting element and a propeller being attached to the distal portion; and (ii) a paddle attached to the cup-shaped surface of the cutting element.

In an embodiment, the part for propelling fluid distally in the tissue collection chamber is a drive shaft having a proximal end and a distal portion, the proximal end being attached to the cutting element and a propeller being attached to the distal portion. In one embodiment, the propeller is located distally of the opening and proximally of the distal end of the collection chamber. In an embodiment, the propeller is located immediately distally of the opening. In an embodiment, the propeller is located in the distal half of the collection chamber. In one embodiment, the proximal end of the drive shaft is attached to a cup-shaped surface of the cutting element, the cup-shaped surface being configured to re-direct tissue cut by the cutting edge in a distal direction when the cup-shaped surface moves in the distal direction.

In an embodiment, the part for propelling fluid distally in the tissue collection chamber is a paddle attached to the cutting element. In an embodiment, the paddle is a wire that is twisted in a helical configuration. In an embodiment, the wire has a rectangular cross section. In an embodiment, the wire has a thickness from 0.002 to 0.020 inch (0.0051 to 0.051 cm). In one embodiment, wire width is from 0.010 to 0.075 inch (0.025 to 0.19 cm). In an embodiment, the paddle has a wire width that is from 20 to 95 percent of an inside diameter of the collection chamber. In an embodiment, the paddle has a longitudinal length that is at least 50 percent of the longitudinal length of the collection chamber. In an embodiment, the paddle has a longitudinal length that is at least 70 percent of the longitudinal length of the collection chamber. In an embodiment, the tissue collection chamber comprises vent holes. In one embodiment, the tissue collection chamber comprises 10 to 200 vent holes. In an embodiment, the vent holes have a diameter of from 25 to 200 microns. In an embodiment, the paddle is attached to a cup-shaped surface of the cutting element, the cup-shaped surface being configured to re-direct tissue cut by the cutting edge in a distal direction when the cup-shaped surface moves in the distal direction.

In one embodiment, the collection chamber comprises a portion at a distal end that can be opened to remove cut material and particles. In an embodiment, the cutting element is movable between a stored position and a cutting position relative to the opening.

The invention provides a method of recirculating fluid in an atherectomy catheter comprising: providing an atherectomy catheter, the atherectomy catheter comprising: a body having an opening; a rotatable shaft coupled to the body; a tissue collection chamber coupled to the body and positioned distal to the cutting element, the tissue collection chamber having vent holes; a cutting element coupled to the rotatable shaft, the cutting element having a cutting edge; and moving fluid out of the tissue collection chamber through the vent holes such that a negative pressure is created inside the tissue collection chamber and this negative pressure causing fluid to enter the tissue collection chamber through the opening of the body of the catheter. In one embodiment, the catheter comprises a lumen configured to direct fluid into the tissue collection chamber. In an embodiment, the catheter comprises a part for propelling fluid distally in the tissue collection chamber, the part being selected from the group consisting of: (i) a drive shaft having a proximal end and a distal portion, the proximal end being attached to the cutting element and a propeller being attached to the distal portion; and (ii) a paddle attached to the cutting element.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft, the cutting element having a cutting edge; and a lumen configured to direct fluid into the tissue collection chamber; placing the catheter in the body lumen; and moving the catheter in the body lumen to contact the cutting element with the material in the body lumen. In one embodiment, the catheter is moved in a distal direction to contact the cutting edge with the material in the body lumen. In one embodiment, the catheter is placed in the body lumen with the cutting element in the stored position and the catheter is moved to contact the material with the cutting element in a cutting position. In one embodiment, the body lumen is a blood vessel.

The invention provides a method of removing material from a body lumen, the method comprising: providing an atherectomy catheter, the atherectomy catheter comprising: a body having an opening; a rotatable shaft coupled to the body; a tissue collection chamber coupled to the body and positioned distal to the cutting element; a cutting element coupled to the rotatable shaft, the cutting element having a cutting edge; and a part for propelling fluid distally in the tissue collection chamber, the part being selected from the group consisting of: (i) a drive shaft having a proximal end and a distal portion, the proximal end being attached to the cutting element and a propeller being attached to the distal portion; and (ii) a paddle attached to the cutting element; placing the catheter in the body lumen; and moving the catheter in the body lumen to contact the cutting element with the material in the body lumen. In one embodiment, the catheter is moved in a distal direction to contact the cutting edge with the material in the body lumen. In one embodiment, the catheter is placed in the body lumen with the cutting element in the stored position and the catheter is moved to contact the material with the cutting element in a cutting position. In one embodiment, the body lumen is a blood vessel.

The present invention provides an improved atherectomy catheter having features for directing particles generated by a cutting element into a collection chamber. Methods of directing the cut material from a blood vessel lumen into a collection chamber are also provided. The cutting element has a sharp cutting edge that surrounds a cup-shaped surface. Cut material is directed into the collection chamber by the cup-shaped surface and by fluid flow.

Referring to FIGS. 1 to 4, an atherectomy catheter 2 is shown which has a cutting element 4, which is used to cut material from a blood flow lumen such as a blood vessel. The cutting element 4 is movable between a stored position (FIG. 2) and a cutting position (FIG. 3) relative to an opening 6 in a body 8 of the catheter 2. The cutting element 4 moves outwardly relative to the opening 6 so that a portion of the element 4 extends outwardly from the body 8 through the opening 6. In one embodiment the cutting element 4 may be positioned relative to the body 8 and opening 6 so that less than 90 degrees of the cutting element 4 is exposed to cut tissue. In other embodiments more of the cutting element 4 may be exposed without departing from numerous aspects of the invention.

Distal end of catheter 2 is positioned near a treatment site of a vessel with cutting element 4 in the stored position. Then catheter 2 is moved distally through the vessel with the cutting element 4 in the working or cutting position as described in further detail below. As the catheter 2 moves through the blood vessel with the cutting element 4 in the working or cutting position the tissue material is cut by the cutting element 4 and is directed into a tissue chamber 12 positioned distal to the cutting element 4. The tissue chamber 12 may be somewhat elongated to accommodate the tissue which has been cut.

To expose cutting element 4 through opening 6, cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

Figure 4:
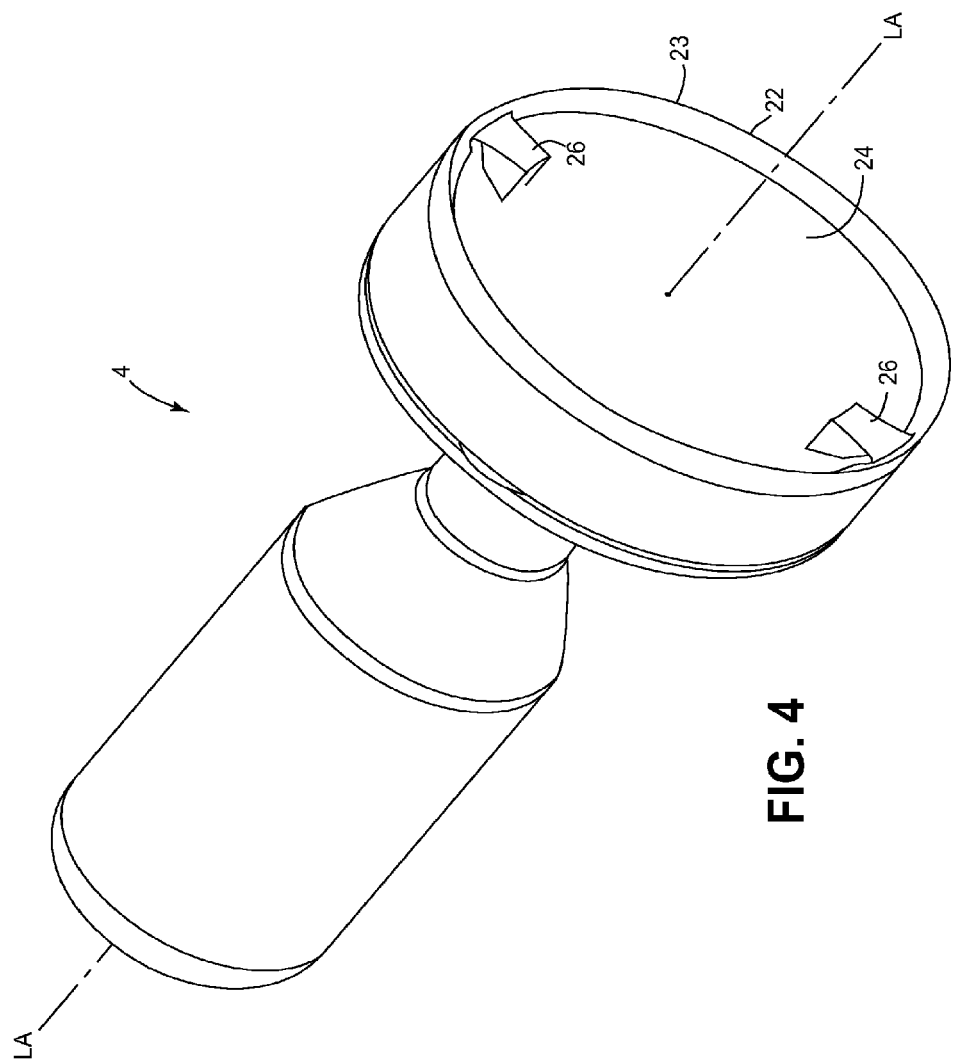
FIG. 4 illustrates an isometric view of an embodiment of a cutting element.

The cutting element 4 has a cup-shaped surface 24, which directs the tissue cut by the cutting edge 22 into the tissue chamber 12. Cutting edge 22 may be at a radially outer edge 23 of the cutting element 4. In some embodiments the cup-shaped surface 24 may be a smooth and continuous surface free of through holes, teeth, fins or other features, which disrupt the smooth nature of the surface 24 for at least half the distance from the longitudinal axis LA to the outer radius at the cutting edge 22. In some embodiments the cup-shaped surface 24 may also be free of any such features throughout an area of at least 300 degrees relative to the longitudinal axis LA. In other embodiments the cup-shaped surface may have a limited amount of through holes, teeth, fins or other features as described in further detail below. One or more raised elements 26 may extend outwardly from the cup-shaped surface 24 with FIG. 4 showing two raised elements 26. The raised element 26 is a small wedge of material that rises relatively abruptly from the cup-shaped surface 24. The raised element 26 helps to break up hard tissue and plaque by applying a relatively blunt striking force to the hard tissue or plaque since cutting such tissue with the cutting edge 22 may not be effective, and strips of such hard tissue may not be flexible enough to be redirected by cup-shaped surface 24 into collection chamber 12. The raised elements 26 altogether occupy a relative small part of the cup-shaped surface 24. By sizing and positioning the raised elements 26 in this manner, the raised elements 26 do not interfere with the ability of the cutting element 4 cup-shaped surface 24 to cut and re-direct large strips of tissue into the tissue chamber while still providing the ability to break up hard tissue and plaque with raised element 26.

The cutting element 4 is coupled to a shaft 20 that extends through a lumen 21 in the catheter 2. Catheter 2 is coupled to exemplary cutter driver 5. Cutter driver 5 is comprised of motor 11, power source 15 (for example one or more batteries), microswitch (not shown), housing 17 (upper half of housing is removed as shown), lever 13 and connection assembly (not shown) for connecting shaft 20 to driver motor 11. Cutter driver 5 can act as a handle for the user to manipulate catheter 2. Lever 13, when actuated to close the microswitch, electrically connects power source 15 to motor 11 thereby causing rotation of cutting element 4. The cutting element 4 is rotated about a longitudinal axis LA when the shaft 20 rotates. The cutting element 4 is rotated at about 1 to 160,000 rpm but may be rotated at any other suitable speed depending upon the particular application. Further description of catheters similar to catheter 2 is found in U.S. Patent Application Publication No. US 2002/0077642 A1 to Patel et. al., entitled "Debulking Catheter", the contents of which are hereby incorporated by reference herein.

In use, catheter 2 cuts softer atheroma from a vessel wall in relatively large strips and cup-shaped surface 24 directs these strips through opening 6 into collection chamber 12. Smaller particles, in some cases produced during the removal of harder or calcified atheroma, can be directed towards opening 6 by the cup-shaped surface 24 and can also be directed tangentially to the spinning cutting element outer edge 23, in some cases past opening 6 and in this event not collected in chamber 12.

Figure 5:
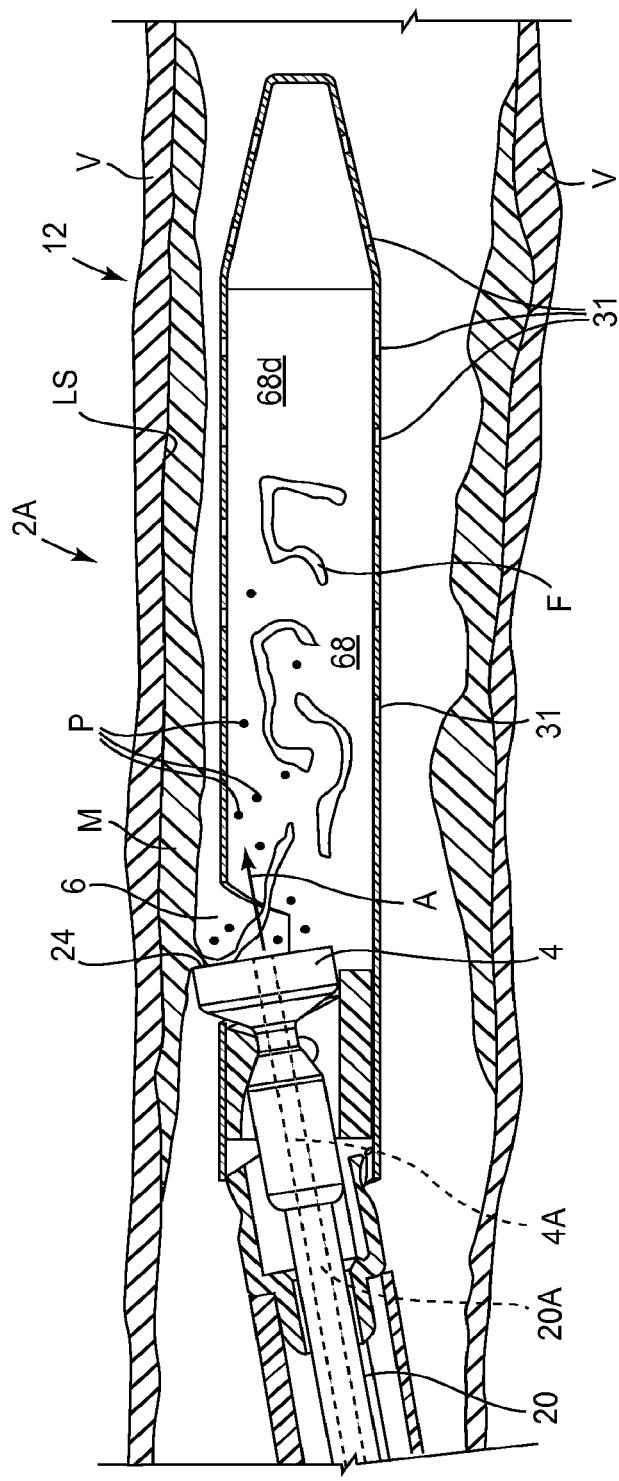
FIGS. 5, 6 and 7 illustrate partial cross-sectional views of distal portions of embodiments of a catheter having improved material collection.

Referring now to FIG. 5, catheter 2A is shown wherein the same or similar reference numbers of catheter 2A refer to the same or similar structures of catheter 2 and all discussion concerning the same or similar features of catheter 2 are equally applicable here unless noted otherwise. Compared to catheter 2, catheter 2A has improved material collection capability and is additionally comprised of lumen 4A in cutting element 4, lumen 20A in connecting shaft 20, rotating fitting at cutter driver 5 (not shown), fluid source (not shown) and vent holes 31 in wall of collection chamber 12. Cutting element 4 and connecting shaft 20 are attached by bonding, welding, molding, pressure fit, gasketed mechanical seal, or other means so as to form a leak-tight fluid connection between lumens 4A and 20A. Rotating fitting at cutter driver 5 is attached to connecting shaft 20 and to fluid source in a similar manner so as to form a fluid tight connection between the fluid source and rotating connecting shaft 20. In some embodiments lumen diameters and lengths are sized so as to permit fluid flow rates of 0.5 to 50 cc/min, including 0.5, 1, 2, 5, 10, 20, or 50 cc/min, or other flow rates at a driving pressure of 50 psi (345 kilopascal). In other embodiments these flow rates are achieved at driving pressures of 1, 5, 10, 20, 100 or 150 psi (6.9, 35, 69, 140, 690, or 1000 kilopascal), or at pressures therebetween.

Vent holes 31 allow fluid to flow out of interior 68 of collection chamber 12 without allowing significant particles of material to pass therethrough. In one embodiment, vent hole diameter is 50 microns. In other embodiments vent hole diameter is from 25 to 200 microns, including 25, 35, 65, 80, 100, 150 or 200 microns. The number, spacing and distribution of vent holes 31 can vary. In various embodiments, 10 to 200 vent holes are contemplated and the number of vent holes can be from 10 to 200, including 10, 20, 30, 50, 75, 100, or 200. The holes can be uniformly or non-uniformly distributed over the outer surface of collection chamber 12. In one embodiment more than half of the holes are distributed over the proximal half of the outer surface of collection chamber 12 so that flow from interior 68 of collection chamber 12 is preserved as holes of the collection chamber become blocked by particles and fragments. In another embodiment, to encourage fluid to preferentially flow out of vent holes 31 as opposed to out of opening 6, the aggregate hydraulic resistance of fluid passing through all vent holes is less than the hydraulic resistance of fluid passing through opening 6.

In operation, catheter 2A is advanced through vessel V with cutting element 4 exposed through opening 6. Cutting element 4 separates large fragments F of atheromatous material M from luminal surface LS of vessel V and cup-shaped surface 24 of cutting element 4 directs said fragments through opening 6 into interior 68 of collection chamber 12. The fluid source forces pressurized fluid (such as physiological saline solution) through lumens 20A, 4A before, during or after rotation of cutting element 4, or any combination of before, during or after rotation of cutting element 4. Fluid exits lumen 4A of cutting element 4 in direction of arrow A and flows into interior 68 of collection chamber 12 and out of vent holes 31. Small particles P, generated by cutting element 4 acting on material M, are carried by fluid flow into distal region 68d of interior 68 of collection chamber 12.

Figure 6:
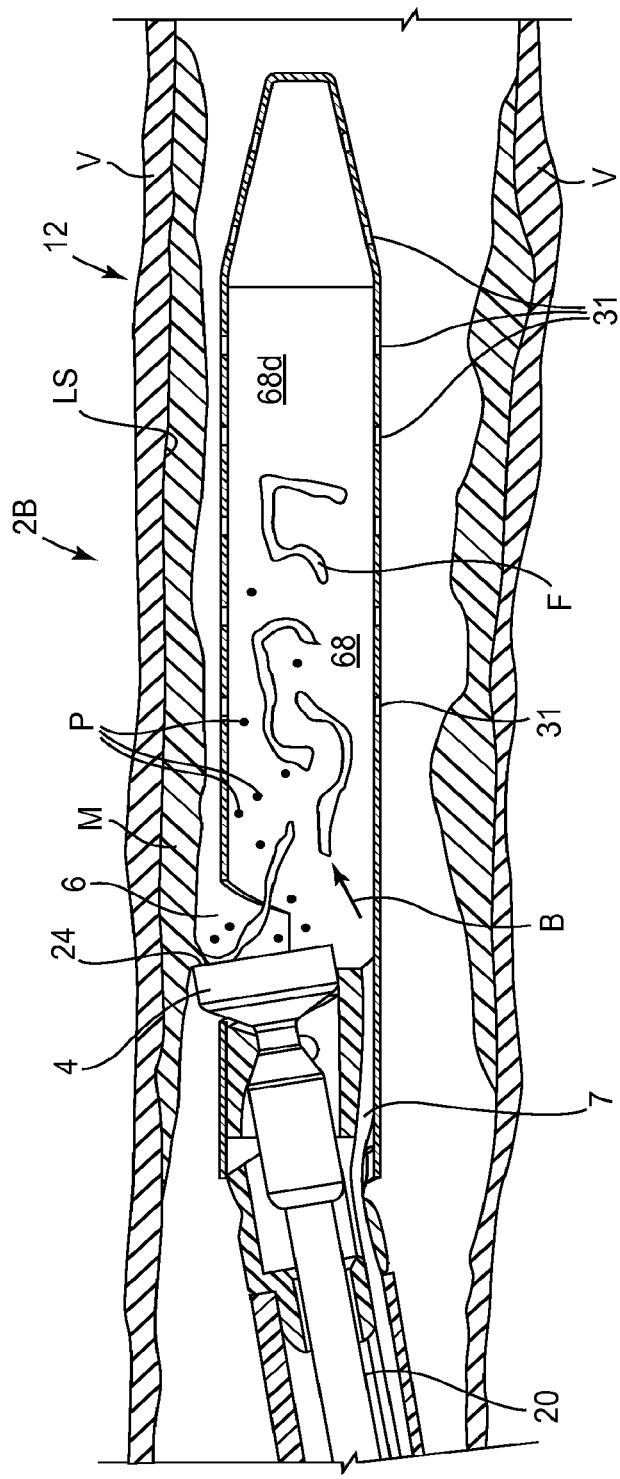

Referring to FIG. 6, another catheter 2B is shown wherein the same or similar reference numbers of catheter 2B refer to the same or similar structures of catheter 2 and all discussion concerning the same or similar features of catheter 2 are equally applicable here unless noted otherwise. Compared to catheter 2, catheter 2B has improved material collection capability and is additionally comprised of tube 7, fluid source (not shown) and vent holes 31 in wall of collection chamber 12. Tube 7 is attached to the fluid source with a leak-tight fluid connection such as a gasketed mechanical seal in the vicinity of cutter driver 5. The fluid source, in some embodiments, provides flow only when cutter 4 is rotating, for example by means of a valve, so as to prevent infusion of excessive fluid into a patient. The fluid source can provide flow before, during or after rotation of cutting element 4, or any combination of before, during or after rotation of cutting element 4. In other embodiments the fluid is comprised of radiopaque substances, such as contrast media, to facilitate visualization of the amount of material within collection chamber 12. The distal end of tube 7 can be oriented in any direction ranging from towards the side wall of collection chamber 12 to towards the distalmost end of collection chamber 12. In one embodiment the distal end of tube 7 is oriented towards distal region 68d of interior 68 of collection chamber 12. In other embodiments tube 7 has a one way valve that allows flow distally through the tube but prevents flow proximally through the tube so as to prevent blood or debris from entering tube 7 and potentially clogging the lumen of tube 7. In some embodiments the lumen diameter and length of tube 7 are sized so as to permit fluid flow rates of 0.5 to 50 cc/min, including 0.5, 1, 2, 5, 10, 20, or 50 cc/min, or other flow rates at a driving pressure of 50 psi (345 kilopascal). In other embodiments these flow rates are achieved at driving pressures of 1, 5, 10, 20, 100 or 150 psi (6.9, 35, 69, 140, 690, or 1000 kilopascal), or at pressures therebetween. Vent holes 31 have structure and functional characteristics as described above for catheter 2A.

In another embodiment of catheter 2B, fluid is infused through lumen 21 of catheter 2 instead of being infused through the lumen of tube 7. In this embodiment fluid passages (not shown) can be provided in ramp 16 such that fluid will flow distally through ramp 16 and exit from ramp 16 into interior 68 of collection chamber 12.

In operation, catheter 2B is advanced through vessel V with cutting element 4 exposed through opening 6. Cutting element 4 separates large fragments F of atheromatous material M from luminal surface LS of vessel V and cup-shaped surface 24 of cutting element 4 directs said fragments through opening 6 into interior 68 of collection chamber 12. The fluid source forces pressurized fluid (such as physiological saline solution) through tube 7 before, during or after rotation of cutting element 4, or any combination of before, during or after rotation of cutting element 4. In some embodiments the fluid is comprised of radiopaque dye and the amount of plaque in the tip is visualized. Fluid exits the lumen of tube 7 in the direction of arrow B and flows into interior 68 of collection chamber 12 and out of vent holes 31. Small particles P, generated by cutting element 4 acting on material M, are carried by fluid flow into distal region 68d of interior 68 of collection chamber 12.

Figure 7:
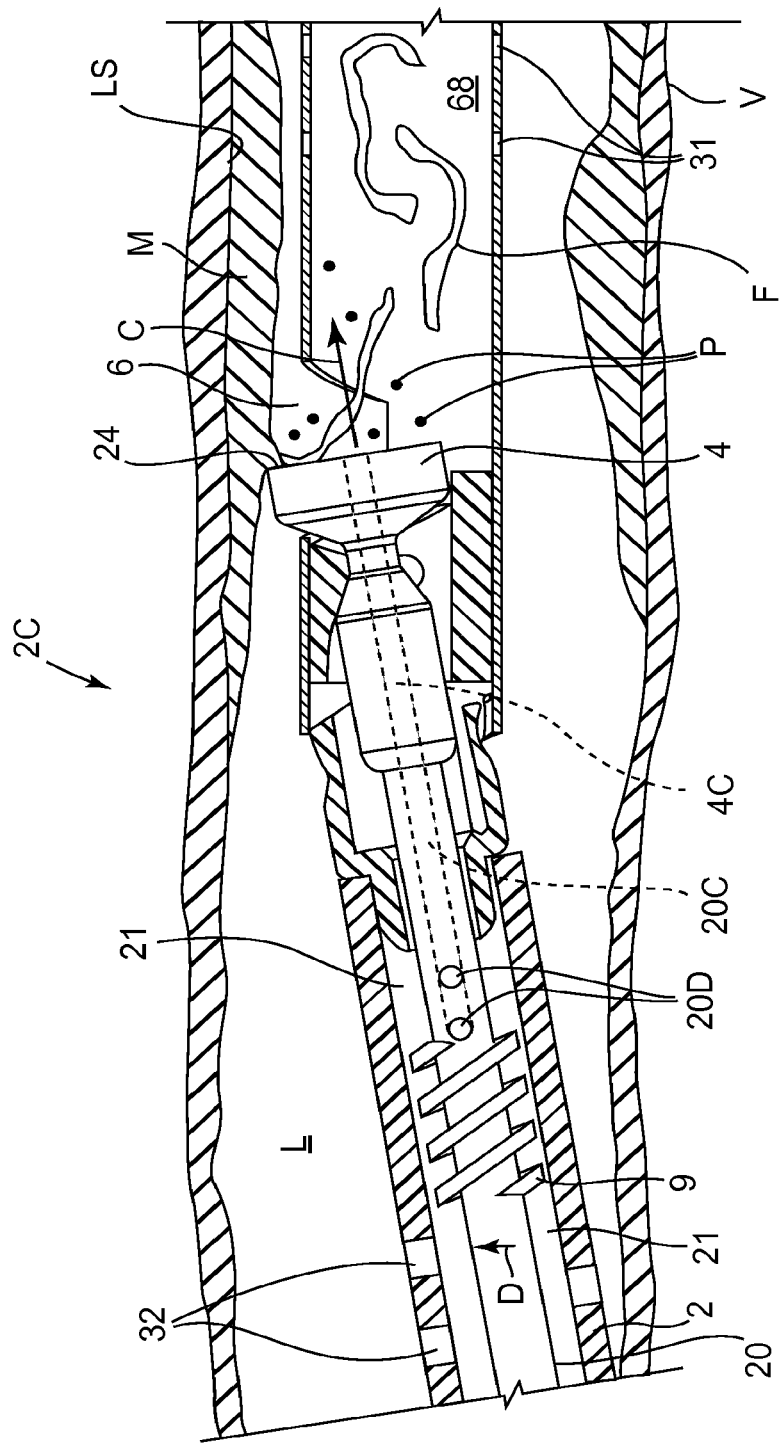

Referring to FIG. 7, another catheter 2C is shown wherein the same or similar reference numbers of catheter 2C refer to the same or similar structures of catheter 2 and all discussion concerning the same or similar features of catheter 2 are equally applicable here unless noted otherwise. Compared to catheter 2, catheter 2C has improved material collection capability and is additionally comprised of lumen 4C in cutting element 4, lumen 20C and holes 20D in connecting shaft 20, impeller 9, inlet holes 32 in catheter 2 and vent holes 31 in the wall of collection chamber 12. Cutting element 4 and connecting shaft 20 are attached by bonding, welding, molding, pressure fit, gasketed mechanical seal, or other means so as to form a leak-tight fluid connection between lumens 4C and 20C. Holes 32 allow passage of fluid from lumen L of vessel V into lumen 21 and holes 20D allow passage of fluid from lumen 21 into lumen 20C. In some embodiments lumen diameters and lengths are sized so as to permit fluid flow rates of 0.5 to 50 cc/min, including 0.5, 1, 2, 5, 10, 20, or 50 cc/min, or other flow rates at a driving pressure of 50 psi (345 kilopascal). In other embodiments these flow rates are achieved at driving pressures of 1, 5, 10, 20, 100 or 150 psi (6.9, 35, 69, 140, 690, or 1000 kilopascal), or at pressures therebetween. Impeller 9 is fixedly attached to connecting shaft 20 by adhesive bond, welding, mechanical interlock, or other means.

Figure 7A:
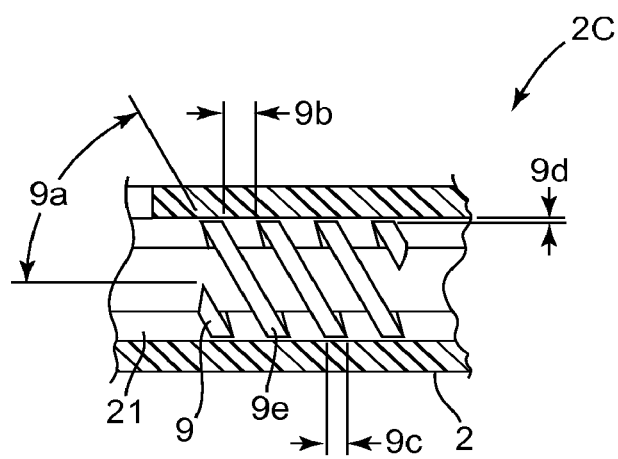
FIG. 7A illustrates a partial cross-sectional side view of a portion of the catheter illustrated in FIG. 7.

Referring to FIG. 7A, impeller 9 is comprised of metal, plastic, or other materials including but not limited to stainless steel, nitinol, polyoxymethylene (commercially available under the trade designation DELRIN®), polyether block amide (commercially available under the trade designation PEBAX®), polyamide, nylon 12, polyester, or other materials. Impeller 9 may be a separately fabricated component that is attached to connecting shaft 20 by welding, adhesive bond, or other means, or may be integrally formed from the shaft. In some embodiments the impeller is comprised of 1 to 10 or more turns, including 1, 2, 3, 4, 6, 8, or 10 turns (four turns 9e are illustrated in FIG. 7A). Pitch angles 9a of 10 to 75 degrees, including 10, 20, 30, 45, 60 or 75 degrees, are contemplated and pitch spacing 9b may be uniform or varied along the length of impeller. Impeller land width 9c may also vary along the length of the impeller. In some embodiments clearance 9d between the outer diameter of impeller 9 and inner diameter of catheter 2 may be from 0.000 to 0.010 inch (0.000 to 0.025 cm), including 0.000, 0.001, 0.002, 0.003, 0.004, 0.007 or 0.010 inch (0.000, 0.0025, 0.0051, 0.0076, 0.010, 0.018 or 0.025 cm) or in amounts therebetween. In other embodiments there may be an interference fit or negative clearance 9d between the outer diameter of impeller 9 and inner diameter of catheter 2 in the amount of from 0.0005 to 0.002 inch (0.0013 to 0.0051 cm), including 0.0005, 0.001 or 0.002 inch (0.0013, 0.0025 or 0.0051 cm) or in amounts therebetween. In further embodiments dimensions of impeller 9 and diameter of lumen 21 may be varied so as to generate fluid flow rates of 0.5 to 50 cc/min, including 0.5, 1, 2, 5, 10, 20, or 50 cc/min, or other flow rates when the impeller is rotating at 1,000, 2,000, 4,000, 8,000, 16,000 or 24,000 RPM or at rotational speeds therebetween. Vent holes 31 have structure and functional characteristics as described above for catheter 2A.

In operation, catheter 2C is advanced through vessel V with cutting element 4 exposed through opening 6. Cutting element separates large fragments F of atheromatous material M from luminal surface LS of vessel V and cup-shaped surface 24 of cutting element 4 directs said fragments through opening 6 into interior 68 of collection chamber 12. Impeller 9, rotating in the direction indicated by arrow D, draws fluid (such as blood) from lumen L of vessel through holes 32 and into lumen 21, pressurizes the fluid and forces the pressurized fluid through holes 20D, lumen 20C and lumen 4C during rotation of cutting element 4. Fluid exits lumen 4C of cutting element 4 in the direction of arrow C and flows into interior 68 of collection chamber 12 and out of vent holes 31. Small particles P, generated by cutting element 4 acting on material M, are carried by fluid flow into distal region 68d of interior 68 of collection chamber 12.

Figure 8A:
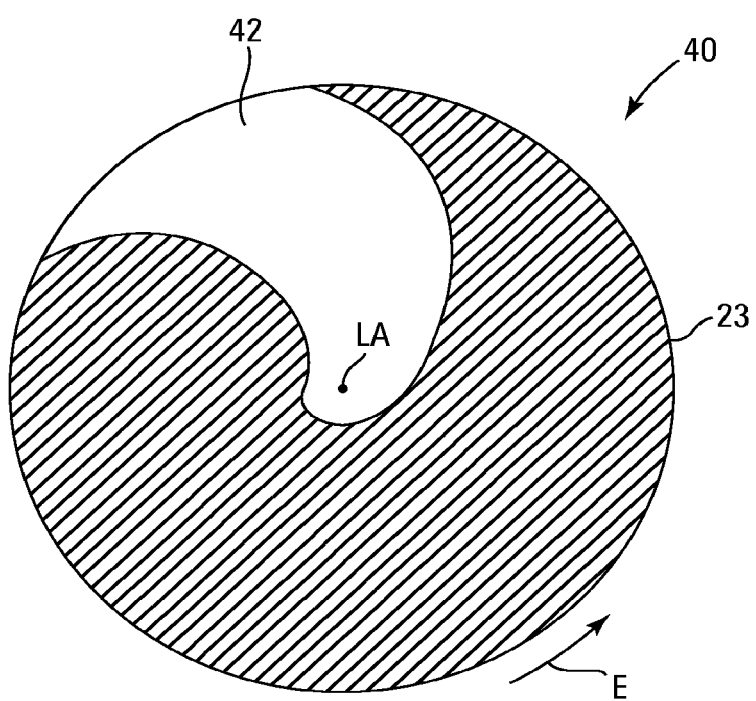
FIG. 8A illustrates a cross sectional view of the cutting element illustrated in FIG. 8.

Cutting element 40 (see FIGS. 8 and 8A) can be used in place of cutting element 4 in any of catheters 2, 2A, 2B, 2C or 2D. Cutting element 40 is similar to cutting element 4 wherein the same or similar reference numbers of cutting element 40 refer to the same or similar structures of cutting element 4 and all discussion concerning the same or similar features of cutting element 4 are equally applicable here unless noted otherwise. Compared to cutting element 4, cutting element 40 is additionally comprised of one or more channels 42 and one or more holes 44. During rotation of cutting element 40 in direction E fluid (such as blood) enters channel 42 at outer edge 23 of cutting element 40 and exits distally through hole 44. Channel 42 and hole 44 can be fabricated into cutter 40 by drilling, electro-discharge machining (EDM), or other means. In one embodiment, cutting element 40 is made in 2 pieces, one with channel 42 cut therein, the other with cutting edge 22, cup-shaped surface 24, raised element 26 (if used) and hole 44 formed therein, the two pieces being subsequently joined together by welding, soldering, brazing, adhesive bonding, mechanical interlock or other means. In some embodiments holes 44 are not positioned along axis LA of cutting element 40. The number of channels and holes, channel widths 42W, channel lengths 42L, and hole 44 diameters may be varied so as to generate fluid flow rates of 0.5 to 50 cc/min, including 0.5, 1, 2, 5, 10, 20 or 50 cc/min, or other flow rates when cutting element 40 is rotating at 1,000, 2,000, 4,000, 8,000, 16,000 or 24,000 RPM or at rotational speeds therebetween.

In operation, cutting element 40 is rotated in the direction of arrow E during use within a vessel V as previously described for, for example, catheter 2A. Cutting element 40 separates large fragments F of atheromatous material M from luminal surface LS of vessel V and cup-shaped surface 24 of cutting element 4 directs said fragments through opening 6 into interior 68 of collection chamber 12. Cutting element 40, rotating in the direction indicated by arrow E, forces fluid (such as blood) from lumen L of vessel V into channel 42 and into hole 44 during rotation of the cutting element. Fluid exits hole 44 of cutting element 40 in the general direction of longitudinal axis LA and flows into interior 68 of collection chamber 12 and out of vent holes 31. Small particles P, generated by cutting element 40 acting on material M, are carried by fluid flow into distal region 68d of interior 68 of collection chamber 12.

Figure 9:
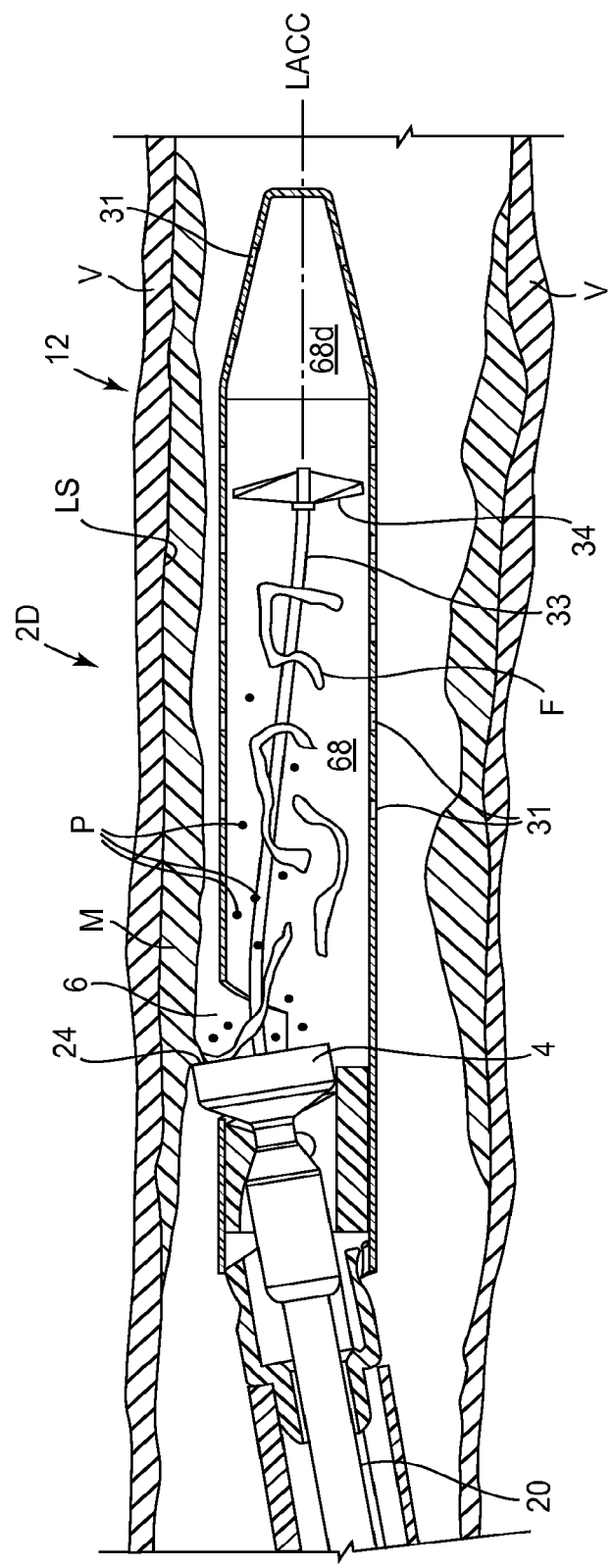
FIG. 9 illustrates a partial cross-sectional view of a distal portion of an embodiment of a catheter having improved material collection.

Referring to FIG. 9, another catheter 2D is shown wherein the same or similar reference numbers of catheter 2D refer to the same or similar structures of catheter 2 and all discussion concerning the same or similar features of catheter 2 are equally applicable here unless noted otherwise. Compared to catheter 2, catheter 2D has improved material collection capability and is additionally comprised of drive shaft 33 and one or more propellers 34. In various embodiments drive shaft 33 and propeller 34 may be comprised of metals such as stainless steel, cobalt-chromium-nickel-molybdenum-iron alloy (commercially available under the trade designation Elgiloy®), or other metals, or polymers such as polyester, polyamide, nylon 12, liquid crystal polymer, or other polymers. Drive shaft 33 is attached to cup-shaped surface 24 of cutting element 4 and propeller 34 is attached to drive shaft 33, in some embodiments by welding, brazing, soldering, overmolding, mechanical interlock, adhesive bonding or other attachment means. In one embodiment, drive shaft 33 is attached to cup-shaped surface 24 of cutting element 4 along longitudinal axis LA. Drive shaft 33 is flexible enough to bend between axis LA of cutting element and the longitudinal axis LACC of collection chamber 12. In one embodiment (FIG. 9) drive shaft 33 is long enough to locate propeller 34 near the distal end of collection chamber 12. In another embodiment (FIG. 10A) drive shaft 33 is only long enough to locate propeller 34 immediately distal to opening 6. Drive shaft 33 may be of any length at or between these two extremes. Propeller 34 is oriented to propel fluid (for example, blood) in a distal direction. The pitch of propeller 34 may be varied so as to generate fluid flow rates of 0.5 to 50 cc/min, including 0.5, 1, 2, 5, 10, 20 or 50 cc/min, or other flow rates when propeller 34 is rotating at 1,000, 2,000, 4,000, 8,000, 16,000 or 24,000 RPM or at rotational speeds therebetween. Vent holes 31 have structure and functional characteristics as described above for catheter 2A.

In operation, catheter 2D is advanced through vessel V with cutting element 4 exposed through opening 6. Cutting element 4 separates large fragments F of atheromatous material M from luminal surface LS of vessel V and cup-shaped surface 24 of cutting element 4 directs said fragments through opening 6 into interior 68 of collection chamber 12. Propeller 34 propels fluid distally in interior 68 of collection chamber 12 and out through vent holes 31, thereby causing fluid (such as blood) to be drawn into collection chamber 12 through opening 6. Fluid flow into opening 6 carries small particles P, generated by cutting element 4 acting on material M, into distal region 68d of interior 68 of collection chamber 12.

Figure 9A:
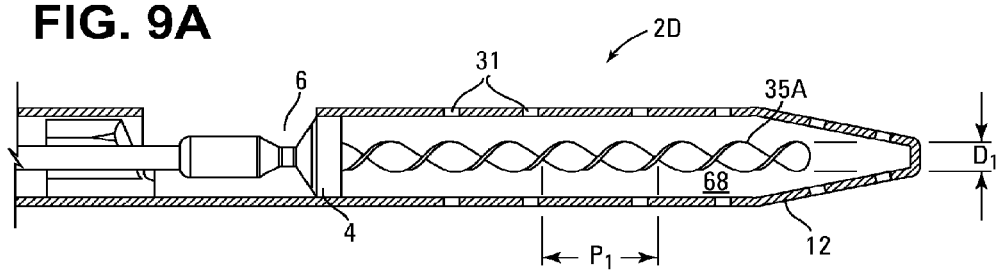
FIGS. 9A, 9B and 9C illustrate partial cross-sectional side views of alternative components for the catheter illustrated in FIG. 9.
Figure 9B:
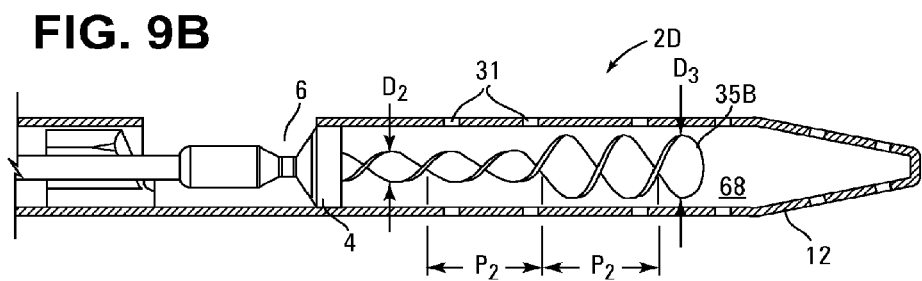
Figure 9C:
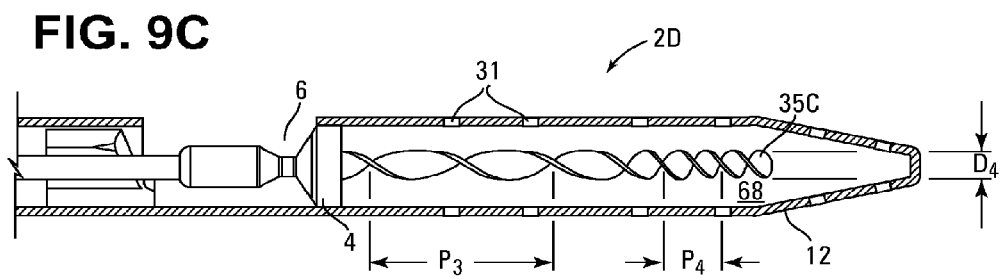

In another embodiment of catheter 2D, a paddle is attached to cup-shaped surface 24 of cutting element 4 instead of attaching drive shaft 33 and propeller 34 to cup-shaped surface 24. Some embodiments of a paddle are illustrated in FIGS. 9A, 9B and 9C and labeled as paddles 35A, 35B and 35C, respectively. The paddles 35A, 35B, 35C are illustrated with cutter 4 in a stored position. The paddles may be comprised of wire having, in some embodiments, a rectangular cross section. The wire is twisted into a helical configuration as shown in the figures. Paddles 35A, 35B, or 35C cause fluid in interior 68 of chamber 12 to move distally during rotation of cutting element 4. In some embodiments wire width (the maximum distance between portions of the wire in the plane perpendicular to the longitudinal axis of the catheter), length and thickness as well as the pitch of the helix may be varied so as to generate fluid flow rates of 0.5 to 50 cc/min, including 0.5, 1, 2, 5, 10, 20, or 50 cc/min, or other flow rates when the impeller is rotating at 1,000, 2,000, 4,000, 8,000, 16,000 or 24,000 RPM or at rotational speeds therebetween. In some embodiments the wire may be from 0.002 to 0.020 inch (0.0051 to 0.051 cm), including 0.002, 0.003, 0.004, 0.005, 0.007, 0.009, 0.011, 0.015 or 0.020 inch (0.0051, 0.0076, 0.010, 0.013, 0.018, 0.023, 0.028, 0.038 or 0.051 cm) thick, and the wire width may be from 0.010 to 0.075 inch (0.025 to 0.19 cm), including 0.010, 0.015, 0.020, 0.025, 0.030, 0.040, 0.050 or 0.075 (0.025, 0.038, 0.051, 0.064, 0.076, 0.10, 0.13 or 0.19 cm), or at thicknesses, wire widths, or both therebetween.

In one exemplary embodiment, FIG. 9A illustrates paddle 35A comprised of rectangular cross section wire that has been twisted into a helix that is nearly as long as the length of collection chamber 12, having a wire width D1 that is 40% of the inside diameter of the collection chamber, and which has a uniform pitch length P1 over the length of the paddle. In another exemplary embodiment, FIG. 9B illustrates paddle 35B comprised of rectangular cross section wire that has been twisted into a helix that is 60% as long as the length of collection chamber 12, having a wire width D2 over the proximal portion of the paddle that is 40% of the inside diameter of the collection chamber and a wire width D3 over the distal portion of the paddle that is 80% of the inside diameter of the collection chamber, and which has a uniform pitch length P2 over the length of the paddle. It is contemplated that other embodiments can have 3 or more different wire widths, or that the wire width may continuously vary over at least portions of paddle 35B. Further, wire widths of from 20% of the inside diameter of the collection chamber to 95% of the inside diameter of the collection chamber are contemplated. FIG. 9C illustrates paddle 35C comprised of rectangular cross section wire that has been twisted into a helix that is 70% as long as the length of collection chamber 12, having a wire width D4 over the length of the paddle that is 30% of the inside diameter of the collection chamber, and a pitch length P3 over a proximal portion of paddle and a pitch length P4 over a distal portion of the paddle. It is contemplated that other embodiments can have 3 or more pitch lengths, or that the pitch length may continuously vary over at least portions of paddle 35C. In yet other embodiments, wire width and pitch length can both vary continuously or discretely over the length of a paddle.

Optionally, in some embodiments catheters 2, 2A, 2B or 2C may additionally be comprised of drive shaft 33 and propeller 34. In other embodiments catheters 2, 2A, 2B or 2C may additionally be comprised of paddles 35A, 35B, or 35C.

In operation, catheter 2D equipped with paddle 35A, 35B, or 35C, instead of shaft 33 and propeller 34, is advanced through vessel V with cutting element 4 exposed through opening 6. Cutting element 4 separates large fragments F of atheromatous material M from luminal surface LS of vessel V and cup-shaped surface 24 of cutting element 4 directs said fragments through opening 6 into interior 68 of collection chamber 12. Paddle 35A, 35B, or 35C propels fluid distally in interior 68 of collection chamber 12 and out through vent holes 31, thereby causing fluid (such as blood) to be drawn into collection chamber 12 through opening 6. Fluid flow into opening 6 carries small particles P, generated by cutting element 4 acting on material M, into distal region 68d of interior 68 of collection chamber 12. Paddle 35 also transports fragments F into distal region 68d of interior 68 of collection chamber 12.

In another embodiment, fragments F and particles P are removed from interior 68 of collection chamber 12 of catheter 2D by providing an opening at the distal end of collection chamber 12 and then rotating propeller 34 or paddle 35 to thereby expel debris. Further description of catheters provided with an opening at the distal end of collection chamber 12 is found in U.S. Patent Application Publication No. US 2005/0222663 A1 to Simpson et. al., entitled "Debulking Catheters and Methods", the contents of which are hereby incorporated by reference herein. See paragraphs [0117] to [0146]. In other embodiments catheters 2, 2A, 2B or 2C may additionally be comprised of shaft 33 and propeller 34 or paddles 35A, 35B, or 35C and the interior of collection chamber 12 may be cleaned of debris as described above for catheter 2D.

Figure 10A:
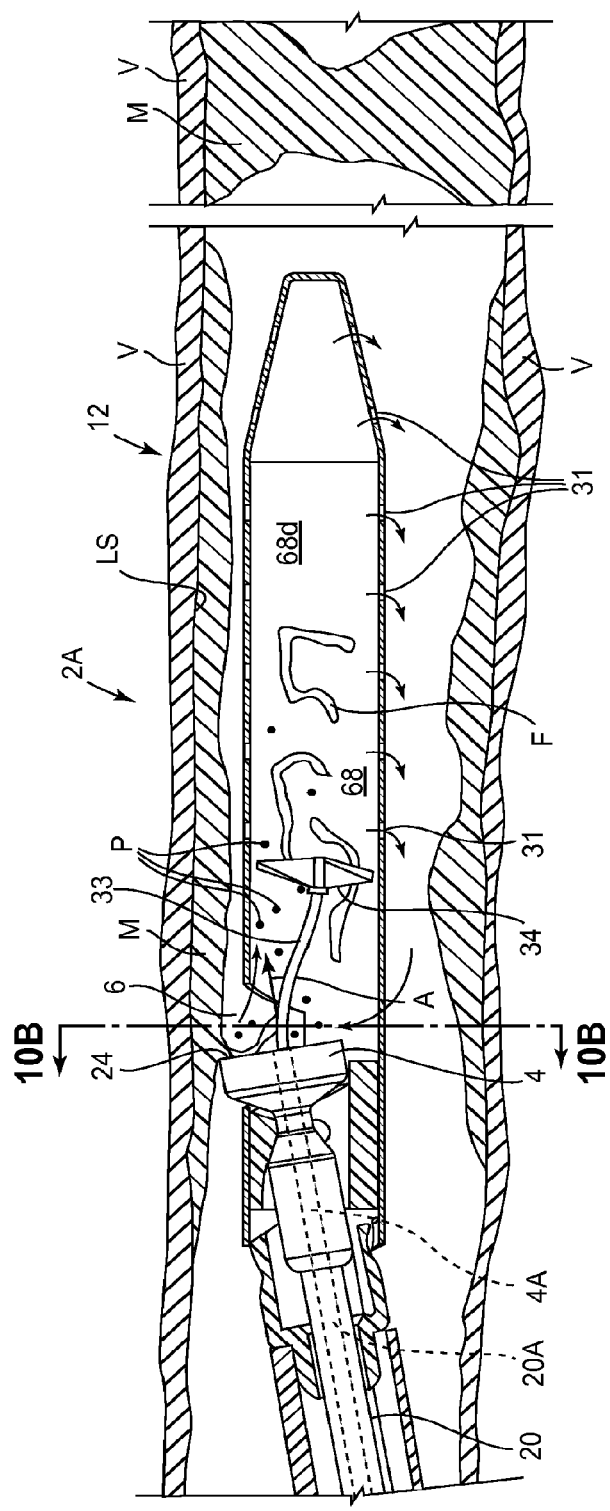
FIGS. 10A and 10B illustrate the catheter illustrated in FIG. 9 in use in a vessel.
Figure 10B:
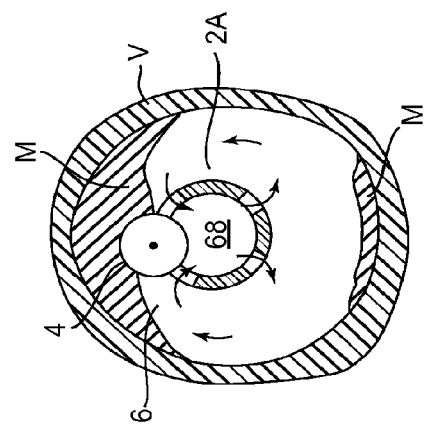

In some embodiments of catheters 2A, 2B, 2C or 2D a fluid recirculation circuit may be established. This is especially desirable in the case of total or near total obstruction of distal runoff in the vessel (see FIG. 10A) where, for example, material M completely occludes the vessel distal to the material removal catheter. To establish a fluid recirculation circuit the flow rate of fluid out of vent holes 31 must exceed the volume of fluid entering into interior 68 of collection chamber 12 through lumen 4A (catheter 2A), through tube 7 (catheter 2B), through lumen 4C (catheter 2C), through hole 44 of cutting element 40, or through combinations of these structures (where used). When this flow condition occurs a negative pressure will be established in the interior 68 of collection chamber 12 and fluid will flow into collection chamber 12 through opening 6, thereby drawing particles P generated by the cutting element into the interior 68 of collection chamber 12 (FIGS. 10A and 10B).

In addition to use in blood vessels the invention is envisioned to be useful for removal of blockages in other blood flow lumens such as natural or artificial grafts, stent-grafts, anastomotic sites, fistulae, or other blood flow lumens.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. An atherectomy catheter, comprising:
    a body having an opening;
    a rotatable shaft coupled to the body;
    a cutting element coupled to the rotatable shaft, the cutting element having a cutting edge;
    a tissue collection chamber coupled to the body and positioned distal to the cutting element; and
    a part for propelling fluid distally in the tissue collection chamber, the part including a drive shaft having a proximal end and a distal portion, and a propeller attached to the distal portion of the drive shaft, wherein the proximal end of the drive shaft is attached to the cutting element.

2. The catheter of claim 1, wherein the cutting element has a cup-shaped surface, the cup-shaped surface being configured to re-direct tissue cut by the cutting edge in a distal direction when the cup-shaped surface moves in the distal direction.

3. The catheter of claim 1, wherein the propeller is located distally of the opening and proximally of a distal end of the collection chamber.

4. The catheter of claim 1, wherein the propeller is located immediately distally of the opening.

5. The catheter of claim 1, wherein the propeller is located in a distal half of the collection chamber.

6. The catheter of claim 1, wherein the proximal end of the drive shaft is attached to a cup-shaped surface of the cutting element, the cup-shaped surface being configured to re-direct tissue cut by the cutting edge in a distal direction when the cup-shaped surface moves in the distal direction.

7. The catheter of claim 1, wherein the tissue collection chamber comprises vent holes.

8. The catheter of claim 7, wherein the tissue collection chamber comprises 10 to 200 vent holes.

9. The catheter of claim 7, wherein the vent holes have a diameter of from 25 to 200 microns.

10. The catheter of claim 1, wherein the collection chamber comprises a portion at a distal end that can be opened to remove cut material and particles.

11. The catheter of claim 1, wherein the cutting element is movable between a stored position and a cutting position relative to the opening.

12. A method of removing material from a body lumen, the method comprising:
    providing an atherectomy catheter, the atherectomy catheter comprising:
        a body having an opening;
        a rotatable shaft coupled to the body;
        a cutting element coupled to the rotatable shaft, the cutting element having a cutting edge;
        a tissue collection chamber coupled to the body and positioned distal to the cutting element; and
        a part for propelling fluid distally in the tissue collection chamber, the part including a drive shaft having a proximal end and a distal portion, and a propeller attached to the distal portion of the drive shaft, wherein the proximal end of the drive shaft is attached to the cutting element;
    placing the catheter in the body lumen; and
    moving the catheter in the body lumen to contact the cutting element with the material in the body lumen.

13. The method of claim 12, wherein the catheter is moved in a distal direction to contact the cutting edge with the material in the body lumen.

14. The method of claim 12, wherein the catheter is placed in the body lumen with the cutting element in the stored position and the catheter is moved to contact the material with the cutting element in a cutting position.

15. The method of claim 12, wherein the body lumen is a blood vessel.

* * * * *